United States Patent [19]

Persinger

[11] Patent Number: 4,932,400

[45] Date of Patent: Jun. 12, 1990

[54] METHOD AND APPARATUS FOR INHIBITING SHIPPING FEVER IN LIVESTOCK AND IMPROVING DIGESTIBILITY OF CONSUMED FEED

[75] Inventor: James G. Persinger, P.O. Box 477, Hugoton, Kans. 67951

[73] Assignee: James Persinger, Hugoton, Kans.

[21] Appl. No.: 205,084

[22] Filed: Jun. 9, 1988

[51] Int. Cl.[5] .......... A61M 15/02

[52] U.S. Cl. .......... 128/202.25; 128/202.16

[58] Field of Search .......... 128/202.25, 202.16; 422/186.12, 186.07; 119/10, 13, 18, 51.01, 72, 74, 156, 50.5

[56] References Cited

U.S. PATENT DOCUMENTS

| | | | |
|---|---|---|---|
| 1,220,160 | 3/1917 | Moore | 422/186.12 |
| 1,376,378 | 4/1921 | Meyenberg | 128/202.25 |
| 2,043,701 | 6/1936 | Hartman | 422/186.08 |
| 2,920,622 | 1/1960 | Steel | 128/202.25 |
| 4,141,830 | 2/1979 | Last | 422/186.12 |
| 4,214,962 | 7/1980 | Pincon | 422/186.12 |
| 4,572,821 | 2/1986 | Brodard et al. | 422/186.12 |
| 4,640,782 | 2/1987 | Burleson | 422/186.12 |

*Primary Examiner*—Edgar S. Burr
*Assistant Examiner*—Aaron J. Lewis
*Attorney, Agent, or Firm*—Frank Frisenda, Jr.

[57] ABSTRACT

The present invention provides a method and apparatus for starting cattle on feed quicker, promoting fill, regaining shrink and help prevent the occurrence of shipping fever complex and promote digestibility and utilization of feedstuffs within the digestive system of ruminant animals, particularly cattle. In a presently preferred embodiment, the inventive method comprises the steps of: producing a gaseous mixture supply of ozone and nitrous oxide gases from ambient air; effecting direct contact between the ozone/nitrous oxide gas mixture and a supply of water by means of a bubbler device to produce a prescribed hydrogen peroxide-nitrous oxide content; continuing said contact between the ozone gas supply and the water supply until the content of hydrogen peroxide-nitrous oxide in water supply is within a range of from about 1,000 parts per million to about 40,000 parts per million; and providing the resultant water supply for use as feed water to the animal to be treated. Accordingly, by consumption of the unique resultant solution, the treated animal has been found to have increased digestibility and utilization of feed and such treatment has found to promote normal rumen function, and inhibit the growth of pathogenic organisms thus inhibiting cattle disease such as shipping fever.

5 Claims, 1 Drawing Sheet

METHOD AND APPARATUS FOR INHIBITING SHIPPING FEVER IN LIVESTOCK AND IMPROVING DIGESTIBILITY OF CONSUMED FEED

BACKGROUND OF THE INVENTION

This invention relates to a method and apparatus for inhibiting disease in livestock and concurrently increasing digestibility and utilization of feed consumed by such livestock.

The occurrence of "shipping fever" (also known as Pasteurella pneumonia and BRDC) has been recognized by those skilled in the art to cause significant dollar loses in feedlots throughout the country. In this respect, it has been estimated that nationwide losses in 1971 were on the order of $20 Million whereas, loss estimates in 1987 approximate $400 Million. *Diseases of Feedlot Cattle*, Colorado State University authored by professor emeritus Dr. Rue Jensen (1971).

Dr. Jensen in the foregoing treatise points out that the disease occurs in cattle of both sexes, 6 to 24 months of age. The incidence of shipping fever is stated to be greatest in late August and during Winter, and usually develops within ten (10) days of an animals' arrival in the feedlot.

Stress factors—weaning, castration, dehorning, vaccination and various environmental considerations -presumably combined to depress the animals' resistance and enhance their susceptibility. The three (3) most common categories of pathogens include the upper respiration viruses, P. haemolytica and P. multocida, combine to cause shipping fever in cattle under such stress.

The bacteria, carried and excreted by some healthy cattle as well as sick animals, can be passed on through ingesting or inhaling infective droplets which may be present in the air, as well as in feed and water.

Both species of Pasteurella can endure for several weeks in moist soil and in dead animal tissue. This is one factor which explains why the disease is widespread throughout all major cattle producing countries.

Recognizing the problems associated with shipping fever, various skilled artisans have proposed systems for prevention. One such system is disclosed in U.S. Pat. No. 3,915,165 issued to Rambosek, et al. on Oct. 28, 1975.

In the described system, Rambosek, et al. disclosed a means for injecting dry medicaments in a gaseous suspension into the trachea of an animal. The system comprises a needle means for insertion into the trachea and a passage way for directing the medicament into the trachea. A mask is formed from substantially gas impermeable material and shaped to fit over the mouth and nose of the animal. Connected to the mask is regulator means for supplying compressed gas to the mask to coincide with the animal's inhalation.

While recognizing that pneumonia ranks as one of the most serious health problems in livestock, the Rambosek system is extremely impractical in that it involves placement of a mask to fit over the animal's nose and mouth which is an impractical matter, is at best an inconvenient and difficult task. Additionally, the Rambosek system involves placement of a needle means inserted into the trachea of the animal which can pose risk factors such as displacement as well as risk of infection from a surgical or puncture wound.

U.S. Pat. No. 4,145,554 issued to Jones, et al., describes various antimicrobial compounds which are stated to be useful for the control of bacterial animal diseases. While helpful in treating bacterial diseases, such compounds generally leave residue in the meat from slaughtered livestock which may deleteriously affect the quality of such meat consumed by ever increasingly health conscious public.

It is generally known that continuous ozone injection into water can inhibit corrosion and control algae and bacteria. In this respect, Humphrey U.S. Pat. No. 4,176,782 discloses ozonation of cooling tower waters. Additionally, other devices for producing ozone are disclosed in U.S. Pat. No. 4,069,153; 4,176,061 and 4,640,783.

One particularly useful apparatus for generating ozone in accordance with the present invention is disclosed in applicants U.S. Pat. No. 4,308,844 issued to James G. Persinger on Jan. 5, 1982 for METHOD AND APPARATUS FOR IMPROVING EFFICIENCY AND COMBUSTION ENGINES. In the Persinger patent, an apparatus is disclosed comprising a tubular ozone generator cell for charging and ionizing a relatively small volume of air. The air supply to the patented generator may be first treated to substantially remove ambient moisture by means of a suitable air dryer or filter. Optionally, a plurality of generators may be connected in sequence to provide an increased source of ozone gas. The disclosure of U.S. Pat. No. 4,308,844 is expressly incorporated herein by this reference.

Accordingly, those skilled in the art, have recognized a significant need for inhibiting the occurrence of shipping fever in cattle, in a convenient economical manner. Further, the need has been recognized to increase digestibility of feed consumed by livestock and to improve utilization of feed stuffs in the rumen. The present invention fulfills these needs.

SUMMARY OF THE INVENTION

The present invention provides a unique method and apparatus for inhibiting the occurrence of shipping fever complex and promote digestibility and utilization of feedstuffs within the digestive system of ruminant animals, particularly cattle.

In a presently preferred embodiment, the inventive method comprises the steps of producing a supply of ozone gas from ambient air; effecting direct contact between the ozone and nitrous oxide gas and a supply of water by means of a bubbler device to produce a prescribed hydrogen peroxide-nitrous oxide content; continuing said contact between the gas supply and the water supply until the content of hydrogen peroxide-nitrous oxide in the water supply is within a range of from about 1,000 parts per million to about 40,000 parts per million; and providing the resultant water supply for use as feed water to the animal to be treated.

Accordingly, by consumption of the unique resultant solution, the treated animal has been found to have increased digestibility of feed and such treatment has found to inhibit the growth of pathogenic organisms thus inhibiting cattle disease such as shipping fever.

Preferably, the apparatus for producing the result in water supply comprises in combination:

Means for filtering a supply of ambient air to substantially remove excessive particle contaminants and excessive moisture;

- Means for directing said air supply from said filter means to ozone generator means for producing a supply of ozone nitrous oxide gas;
- Means for effecting direct contact between said ozone gas and a supply of water by means of a bubbler device;
- Containment means for containing and for providing continuous direct contact between said gas supply and said water supply until the content of hydrogen peroxide-nitrous oxide in the water supply within a range from about one thousand parts per million to about forty thousand parts per million of hydrogen peroxide and nitrous oxide; and
- Means for directing said resultant water supply for use as feed water to an animal to be treated.

The resultant water supply containing hydrogen peroxide and nitrous oxide in its prescribed range has been found to promote the growth of non-pathogenic micro organisms, thus inhibiting the growth of pathogenic micro organisms and to allow the treated animals natural immune system to defend the animal against pathogenic organisms. Optionally, a plurality of ozone generators may be connected in sequence to provide an increase source of gas and with proper containment, form a breathing room system for the livestock to be treated. Moreover, the unique resultant solution has been found to promote the growth of normal non-pathogenic micro organisms within the digestive system and thus reactivate the rumen. Thus, in the preferred mode, the animal with congested lungs will receive treatment via the feed water produced by the ozone generator as well as allowed to inhale the resultant vapors bubbled through water in a breathing room for at least two hours per day.

Additionally objects and features of the present invention will be apparent from the following description with reference to the accompanying drawings and claims.

DESCRIPTION OF THE PREFERRED EMBODIMENTS

The present invention provides a method and apparatus for inhibiting the occurrence of shipping fever complex and digestibility and utilization of feedstuffs within the digestive system of animals, particularly cattle. In a presently preferred embodiment, the inventive method comprises the steps of: producing a supply of ozone-nitrous oxide gas from ambient air; effecting direct contact between the ozone gas and a supply of water by means of a bubbler device to produce a prescribed hydrogen peroxide-nitrous oxide content; continuing said contact between the gas supply and the water supply until the content of hydrogen peroxide-nitrous oxide in the water supply is within a range of from about 1,000 parts per million to about 40,000 parts per million; and providing the resultant water supply for use as feed water to the animal to be treated. Accordingly, by consumption of the unique resultant solution, the treated animal has been found to have increased digestibility of feed and such treatment has found to promote the growth of normal non-pathogenic organisms thus inhibiting cattle disease such as shipping fever.

It has also been found that the unique resultant product in accordance with the present invention decreases the growth of micro organisms in the livestock water tank, thus decreasing the need for cleaning and maintenance of livestock watering mechanisms. Further, the apparatus compromised of the ozone generator may be suitably positioned within a few feet of the livestocks' drinking water.

Figure 1:
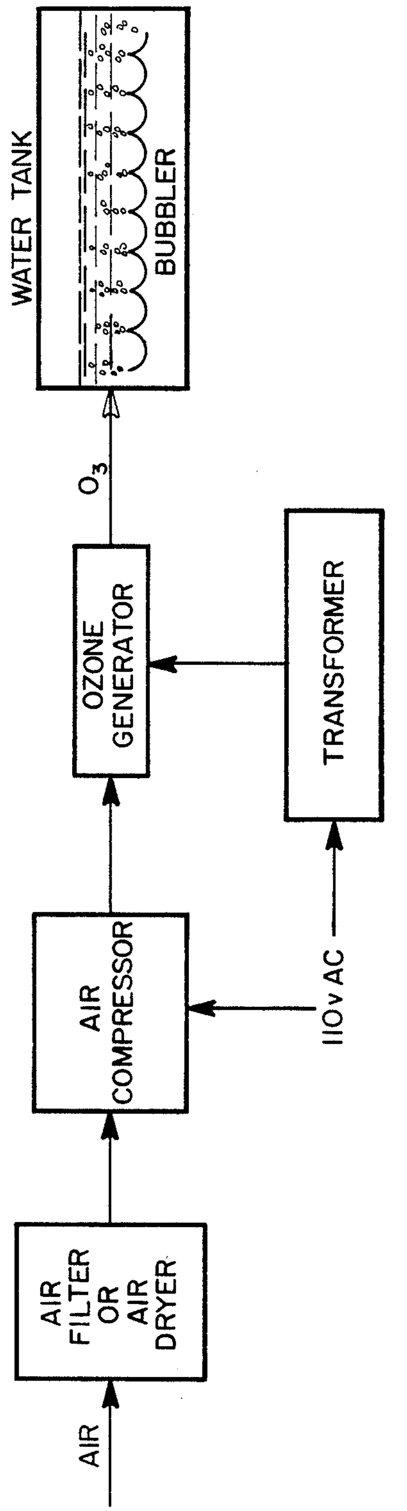
FIG. 1 is a schematic block diagram of one embodied method for inhibiting the occurrence of shipping complex and promoting digestibility and utilization of feedstuffs in accordance with the present invention.
Figure 2:
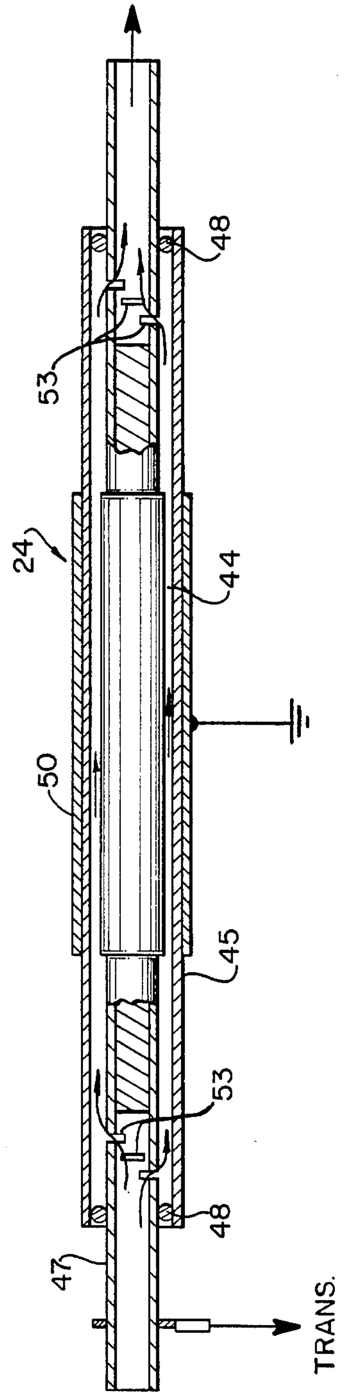
FIG. 2 is cross-sectional view of one suitable device for the production of ozone gas from ambient air in accordance with the present invention.

In more detail, one suitable ozone generator means is disclosed in applicants U.S. Pat. No. 4,308,844 issued to Persinger on Jan. 5, 1982. The apparatus, shown in FIG. 1, compromises an ozone generator cell 24 which acts on ambient air supply. The generator cell 24 produces ozone and nitrous oxide in the air supply and induces a positive charge on portions of such supply. The generator cell 24 compromises metallic plates 47 and 50 disposed adjacent to one another and separated from each other by a dialectic material 45 and an air gap 44.

A potential is induced across the adjacent plates 47 and 50 causing ionization of oxygen and nitrogen in the air flowing through the gap 44 which results in the production of ozone gas, nitrous oxide and ionizing air particles thus producing a gaseous mixture having a positive charge.

In accordance with the present invention, the generator cell 24 produces ozone and nitrous oxide within the air supply and induces a charge of the mixture by applying an alternating potential of 70,000 volts across the plates 47 and 50. The potential across the gap 44, alternating at a frequency in a range from about 200 to 400 cycles per second, produces ozone gas, nitrous oxide and adds positive charges to the portions of air supply.

As described above, the present invention may compromise two or more generator cells sequentially connected to produce the desired amount of gas.

One suitable ignition transformer for use with the ozone cell is available from Dongan Electric Manufacturing Company, of Detroit, Mich. The specifications for the preferred ignition transformer is from about 5,000 volts to about 1,500 volts and preferably, has 10,000 volts production at 60 cycle.

If the ambient air is excessively wet, or contained polluting particulants, an air dryer and/or air filter my be used to remove successive component prior to being fed into a compressor or air mover which flows the supply of air to the ozone generator cell.

Typically, the air supplied to the generator cells should have a minimum flow rate of about one cubic foot per minute, and may have a maximum flow rate of about 4 cubic feet per minute per ozone generator cell. One suitable compressor for this purpose is commercially available from Gast Manufacturing, of Bent Harbor, Mich.

After exiting the ozone generator, the supply of the ozone-nitrous oxide gas is directed to a water tank bubbler for effecting direct contact with a supply of water. One suitable water tank bubbler is commercially available from Porex Technology of Fairbourne, Ga. Preferably, the bubbler will produce a relatively small bubble of ozone nitrous oxide mixture for effecting the direct contact, and twenty to about forty microns is preferred for the bubblers specifications.

Any suitable containment means such as a water tank can be used for containment in effecting the prescribed contact between the ozone-nitrous oxide gas supply and water supply to produce the resultant water mixture having about 1,000 parts per million to about 40,000 per million of hydrogen peroxide-nitrous oxide.

Accordingly, the present invention provides a method and apparatus for inhibiting the occurrences of shipping fever complex and promoting the growth of normal rumen microflora within the digestive system of ruminant animals, particularly cattle.

I claim:

1. A method for inhibiting shipping fever in livestock and improving digestibility of consumed feed, said method comprising the steps of:

producing a gaseous mixture supply of ozone and nitrous oxide gas from ambient air;

effecting direct contact between said gaseous mixture and a supply of water to produce a solution of hydrogen peroxide/nitrous oxide content in said water;

continuing said contact between said gaseous mixture and said water supply until the content of hydrogen peroxide and nitrous oxide in said water supply is within a range of from about 1,000 parts per million to 40,000 parts per million; and providing the resultant water supply for use as feed water to the animal to be treated.

2. The method as defined in claim 1 wherein said method further comprises the step of allowing said animal to be further treated by inhalation of excess gaseous vapors from said water supply in a confined environment for at least two hours per day.

3. The method as defined in claim 1 wherein said gaseous mixture of ozone gas and nitrous oxide gas is produced by an ozone generator cell.

4. The method as defined in claim 3 wherein said gaseous mixture of ozone gas and nitrous oxide is effected by two or more generator cells sequentially connected to produce said gaseous supply.

5. A method of inhibiting shipping fever in livestock and improving digestibility of consume feed, said method comprising the steps of:

(a) producing a gaseous mixture supply of ozone and nitrous oxide gas from ambient air;

(b) effecting direct contact between said gaseous mixture derived from step (a) and a supply of water by means of a bubbler device to produce a solution of hydrogen peroxide/nitrous oxide content in said supply of water;

(c) continuing said contact between said gaseous mixture and said water supply until the content of hydrogen peroxide and nitrous oxide in said water supply is within a range of from about 1,000 parts per million to 40,000 parts per million; and (d) providing the resultant water supply from step (c) for use as feed water to the animal to be treated.

* * * * *